United States Patent [19]

Zocchi et al.

[11] Patent Number: 5,719,114
[45] Date of Patent: Feb. 17, 1998

[54] CLEANING COMPOSITION IN VARIOUS LIQUID FORMS COMPRISING ACARICIDAL AGENTS

[75] Inventors: Germaine Zocchi, Villers aux Tours, Belgium; Betty Kong, Westfield, N.J.; Marianne Mahieu, Ferrieres, Belgium

[73] Assignee: Colgate Palmolive Company, Piscataway, N.J.

[21] Appl. No.: 671,470

[22] Filed: Jun. 28, 1996

[51] Int. Cl.$^6$ .................. C11D 3/48; C11D 3/50; C11D 3/60
[52] U.S. Cl. .......... 510/383; 510/102; 510/107; 510/386; 510/417; 510/421; 510/424; 510/434; 510/437; 510/491; 510/505; 510/506
[58] Field of Search ................ 510/417, 383, 510/421, 422, 427, 432, 102, 104, 106, 107, 386, 424, 437, 491, 505, 506

[56] References Cited

U.S. PATENT DOCUMENTS

| | | | |
|---|---|---|---|
| 2,560,839 | 7/1951 | Ayo et al. | 252/109 |
| 3,234,138 | 2/1966 | Carroll et al. | 252/110 |
| 3,350,319 | 10/1967 | Schonfeldt | 252/138 |
| 3,723,330 | 3/1973 | Sheflin | 252/153 |
| 3,935,130 | 1/1976 | Hirano et al. | 252/542 |
| 4,017,409 | 4/1977 | Demessemasken | 252/109 |
| 4,244,840 | 1/1981 | Straw | 252/540 |
| 4,313,847 | 2/1982 | Chasin et al. | 252/356 |
| 4,414,128 | 11/1983 | Goffinet | 252/111 |
| 4,450,448 | 5/1984 | Gautier et al. | 148/6.15 R |
| 4,472,291 | 9/1984 | Rosano | 252/186.28 |
| 4,540,505 | 9/1985 | Frazier | 252/174.12 |
| 4,564,632 | 1/1986 | Nonn et al. | 514/522 |
| 4,666,940 | 5/1987 | Bischoff et al. | 514/544 |
| 4,737,520 | 4/1988 | Naik et al. | 514/520 |
| 4,804,683 | 2/1989 | Steltenkamp | 514/629 |
| 4,954,338 | 9/1990 | Mattox | 514/372 |
| 5,082,584 | 1/1992 | Loth et al. | 252/122 |
| 5,143,900 | 9/1992 | Steltenkamp | 512/26 |
| 5,403,509 | 4/1995 | Pujol et al. | 510/535 |
| 5,529,713 | 6/1996 | Gauthier-Fournier | 510/384 |
| 5,578,250 | 11/1996 | Thomas et al. | 510/365 |
| 5,610,130 | 3/1997 | Thomas et al. | 510/383 |

FOREIGN PATENT DOCUMENTS

| | | |
|---|---|---|
| 080749 | 6/1983 | European Pat. Off. . |
| 137615 | 4/1985 | European Pat. Off. . |
| 137616 | 4/1985 | European Pat. Off. . |
| 160762 | 11/1985 | European Pat. Off. . |
| 3-269097 | 11/1991 | Japan . |
| 1223739 | 3/1971 | United Kingdom . |
| 2144763 | 3/1985 | United Kingdom . |
| 89/12673 | 12/1989 | WIPO . |

*Primary Examiner*—Ardith Hertzog
*Attorney, Agent, or Firm*—Richard E. Nanfeldt; James Serafino

[57] ABSTRACT

The present invention relates to a light duty liquid, microemulsion, hard surface cleaning or liquid composition containing 0.05 to 5.0 wt. % of an acaricidal agent.

14 Claims, No Drawings

CLEANING COMPOSITION IN VARIOUS LIQUID FORMS COMPRISING ACARICIDAL AGENTS

FIELD OF THE INVENTION

This invention relates to an improved all-purpose liquid cleaner containing an acaricidal agent which can be in the form of a liquid crystal or a microemulsion designed in particular for cleaning hard surfaces and which is effective in killing dust mites and removing grease soil and/or bath soil and in leaving unrinsed surfaces with a shiny appearance.

BACKGROUND OF THE INVENTION

In recent years all-purpose liquid detergents have become widely accepted for cleaning hard surfaces, e.g., painted woodwork and panels, tiled walls, wash bowls, bathtubs, linoleum or tile floors, washable wall paper, etc. Such all-purpose liquids comprise clear and opaque aqueous mixtures of water-soluble synthetic organic detergents and water-soluble detergent builder salts. In order to achieve comparable cleaning efficiency with granular or powdered all-purpose cleaning compositions, use of water-soluble inorganic phosphate builder salts was favored in the prior art all-purpose liquids. For example, such early phosphate-containing compositions are described in U.S. Pat. Nos. 2,560,839; 3,234,138; 3,350,319; and British Patent No. 1,223,739.

In view of the environmentalist's efforts to reduce phosphate levels in ground water, improved all-purpose liquids containing reduced concentrations of inorganic phosphate builder salts or non-phosphate builder salts have appeared. A particularly useful self-opacified liquid of the latter type is described in U.S. Pat. No. 4,244,840.

However, these prior art all-purpose liquid detergents containing detergent builder salts or other equivalent tend to leave films, spots or streaks on cleaned unrinsed surfaces, particularly shiny surfaces. Thus, such liquids require thorough rinsing of the cleaned surfaces which is a time-consuming chore for the user.

In order to overcome the foregoing disadvantage of the prior art all-purpose liquid, U.S. Pat. No. 4,017,409 teaches that a mixture of paraffin sulfonate and a reduced concentration of inorganic phosphate builder salt should be employed. However, such compositions are not completely acceptable from an environmental point of view based upon the phosphate content. On the other hand, another alternative to achieving phosphate-free all-purpose liquids has been to use a major proportion of a mixture of anionic and nonionic detergents with minor amounts of glycol ether solvent and organic amine as shown in U.S. Pat. No. 3,935,130. Again, this approach has not been completely satisfactory and the high levels of organic detergents necessary to achieve cleaning cause foaming which, in turn, leads to the need for thorough rinsing which has been found to be undesirable to today's consumers.

Another approach to formulating hard surfaced or all-purpose liquid detergent composition where product homogeneity and clarity are important considerations involves the formation of oil-in-water (o/w) microemulsions which contain one or more surface-active detergent compounds, a water-immiscible solvent (typically a hydrocarbon solvent), water and a "cosurfactant" compound which provides product stability. By definition, an o/w microemulsion is a spontaneously forming colloidal dispersion of "oil" phase particles having a particle size in the range of 25 Å to 800 Å in a continuous aqueous phase.

In view of the extremely fine particle size of the dispersed oil phase particles, microemulsions are transparent to light and are clear and usually highly stable against phase separation.

Patent disclosures relating to use of grease-removal solvents in o/w microemulsions include, for example, European Patent Applications EP 0137615 and EP 0137616—Herhots et al; European Patent Application EP 0160762—Johnston et al; and U.S. Pat. No. 4,561,991—Herbots et al. Each of these patent disclosures also teaches using at least 5% by weight of grease-removal solvent.

It also is known from British Patent Application GB 2144763A to Herbots et al, published Mar. 13, 1985, that magnesium salts enhance grease-removal performance of organic grease-removal solvents, such as the terpenes, in o/w microemulsion liquid detergent compositions. The compositions of this invention described by Herbots et al. require at least 5% of the mixture of grease-removal solvent and magnesium salt and preferably at least 5% of solvent (which may be a mixture of water-immiscible non-polar solvent with a sparingly soluble slightly polar solvent) and at least 0.1% magnesium salt.

However, since the amount of water immiscible and sparingly soluble components which can be present in an o/w microemulsion, with low total active ingredients without impairing the stability of the microemulsion is rather limited (for example, up to 18% by weight of the aqueous phase), the presence of such high quantities of grease-removal solvent tend to reduce the total amount of greasy or oily soils which can be taken up by and into the microemulsion without causing phase separation.

The following representative prior art patents also relate to liquid detergent cleaning compositions in the form of o/w microemulsions: U.S. Pat. Nos. 4,472,291—Rosario; 4,540,448—Gauteer et al; 3,723,330—Sheflin; etc.

Liquid detergent compositions which include terpenes, such as d-limonene, or other grease-removal solvent, although not disclosed to be in the form of o/w microemulsions, are the subject matter of the following representative patent documents: European Patent Application 0080749; British Patent Specification 1,603,047; 4,414,128; and 4,540,505. For example, U.S. Pat. No. 4,414,128 broadly discloses an aqueous liquid detergent composition characterized by, by weight:

(a) from 1% to 20% of a synthetic anionic, nonionic, amphoteric or zwitterionic surfactant or mixture thereof;

(b) from 0.5% to 10% of a mono- or sesquiterpene or mixture thereof, at a weight ratio of (a):(b) lying in the range of 5:1 to 1:3; and (c) from 0.5% 10% of a polar solvent having a solubility in water at 15° C. in the range of from 0.2% to 10%. Other ingredients present in the formulations disclosed in this patent include from 0.05% to 2% by weight of an alkali metal, ammonium or alkanolammonium soap of a $C_{13}$–$C_{24}$ fatty acid; a calcium sequestrant from 0.5% to 13% by weight; non-aqueous solvent, e.g., alcohols and glycol ethers, up to 10% by weight; and hydrotropes, e.g., urea, ethanolamines, salts of lower alkylaryl sulfonates, up to 10% by weight. All of the formulations shown in the Examples of this patent include relatively large amounts of detergent builder salts which are detrimental to surface shine.

Furthermore, the present inventors have observed that in formulations containing grease-removal assisting magnesium compounds, the addition of minor amounts of builder salts, such as alkali metal polyphosphates, alkali metal carbonates, nitrilotriacetic acid salts, and so on, tends to make it more difficult to form stable microemulsion systems.

U.S. Pat. No. 5,082,584 discloses a microemulsion composition having an anionic surfactant, a cosurfactant, nonionic surfactant, perfume and water; however, these compositions do not possess the low ecotoxicity profile and the improved interfacial tension properties as exhibited by the compositions of the instant invention.

British Patent No 1,453,385 discloses polyesterified nonionic surfactants similar to the polyesterified nonionic surfactants of the instant invention. However, these nonionic surfactants of British Patent 1,453,385 do not disclose the formula (II) portion of the instant composition. Additionally, the formulated compositions of British Patent 1,453,385 fail to disclose the critical limitations of the instant invention.

A number of patents teach esterified ethoxylated glycerol compounds for various applications. These patents are Great Britian 1,453,385; Japan 59-1600 and Japan 58-206693 and European Patent Application 0586,323A1. These publications fail to appreciate that a mixture of esterified ethoxylated glycerol and nonesterified ethoxylated glycerol, when used in a hard surface cleaning composition, functions as a grease release agent.

U.S. Pat. No. 4,666,940 discloses acaricidal agents in combination with solid components that leave a residue on the surface being treated.

SUMMARY OF THE INVENTION

The present invention provides an improved, clear, liquid cleaning composition containing an acaricidal agent which can be in the form of a liquid crystal or a microemulsion. The composition is suitable for cleaning hard surfaces such as plastic, vitreous and metal surfaces having a shiny finish. More particularly, the improved cleaning compositions exhibit acaricidal activity and good grease soil removal properties due to the improved interfacial tensions, when used in undiluted (neat) form and leave the cleaned surfaces substantially free of dust mites and shiny without the need of or requiring only minimal additional rinsing or wiping. The latter characteristic is evidenced by little or no visible residues on the unrinsed cleaned surfaces and, accordingly, overcomes one of the disadvantages of prior art products. The instant compositions besides killing dust mites exhibit a grease release effect in that the instant compositions impede or decrease the anchoring of greasy soil on surfaces that have been cleaned with the instant compositions as compared to surfaces cleaned with a liquid crystal composition or a commercial microemulsion composition which means that the grease soiled surface is easier to clean upon subsequent cleanings. Surprisingly, these desirable results are accomplished even in the absence of polyphosphate or other inorganic or organic detergent builder salts and also in the complete absence or substantially complete absence of grease-removal solvent.

In one aspect, the invention generally provides a stable, clear all-purpose, hard surface cleaning composition especially effective in killing dust mites and in the removal of oily and greasy oil. The instant composition which can be an all purpose hard surface cleaning composition, a microemulsion cleaning or a light duty liquid cleaning composition comprises on a weight basis:

from 0 to 20% of an anionic surfactant;

0 to 10% of a zwitterionic surfactant;

from 0 to 20% of a water-mixable cosurfactant having either limited ability or substantially no ability to dissolve oily or greasy soil;

0.1% to 20% of a nonionic surfactant or a compound which is a mixture of a partially esterified ethoxylated polyhydric alcohol, a fully esterified ethoxylated polyhydric alcohol and a nonesterified ethoxylated polyhydric alcohol, said mixture being (herein after referred to as an ethoxylated glycerol type compound) and mixtures thereof;

0 to 5% of magnesium sulfate heptahydrate;

0 to 10% of a perfume, essential oil or water insoluble hydrocarbon;

0.05% to 5.0% of at least one acaricidal agent; and the balance being water, said proportions being based upon the total weight of the composition, wherein the composition does not contain a solid component having a mean particle size of 2 to 100 microns which would leave a pulverulent residue on the surface being treated or quartz, sand, siliceous earth, metal carbonate, $SiO_2$, amorphous silica, silicates, polyacrylates or xanthan gum.

Quite surprisingly although the perfume is not, per se, a solvent for greasy or oily soil,—even though some perfumes may, in fact, contain as much as 80% of terpenes which are known as good grease solvents—the inventive compositions in dilute form have the capacity to solubilize up to 10 times or more of the weight of the perfume of oily and greasy soil, which is removed or loosened from the hard surface by virtue of the action of the anionic and nonionic surfactants, said soil being taken up into the oil phase of the o/w microemulsion.

The invention generally provides highly concentration microemulsion compositions in the form of either an oil-in-water (o/w) microemulsion or a water-in-oil (w/o) microemulsion which when diluted with additional water before use can form dilute o/w microemulsion compositions. Broadly, the concentrated microemulsion compositions contain, by weight, 1% to 30% of an anionic surfactant, 0.05% to 5.0% of at least one acaricidal agent; 0.6% to 20% of a nonionic surfactant and/or an ethoxylated glycerol type compound, 0% to 2.5% of a fatty acid, 0.4 to 10% of perfume, essential oil or water insoluble hydrocarbon having 6 to 18 carbon atoms, 0.1% to 20% of a cosurfactant, and 20% to 97% of water.

The instant compositions are also related to liquid crystal compositions which comprise by weight 0% to 20% of an anionic surfactant, 0.1% to 20% of a nonionic surfactant and/or an ethoxylated glycerol type compound, 0.05% to 5.0% of an acaricidal agent, 0 to 2.5% of a fatty acid, 0.5% to 10% of a perfume, essential oil or water insoluble hydrocarbon, 1% to 20% of cosurfactant and the balance being water.

DETAILED DESCRIPTION OF THE INVENTION

The present invention relates to a stable liquid crystal, all purpose hard surface cleaning or microemulsion compositions comprising approximately by weight: 0.1% to 20% of an anionic surfactant, 0.05% to 5.0% of an acaricidal agent, 0 to 20% of a cosurfactant, 0.1% to 20% of a nonionic surfactant and/or an ethoxylated glycerol type compound, 0 to 10% of a water insoluble hydrocarbon, essential oil or a perfume and the balance being water, wherein the composition does not contain a solid component having a mean particle size of 2 to 100 microns which would leave a pulverulent residue on the surface being treated or quartz, sand, siliceous earth, metal carbonate, $SiO_2$, amorphous silica, silicates, polyacrylates, xanthan gum.

The present invention also relates to a light duty liquid cleaning composition comprising approximately by weight: 10 to 40% of at least organic compound selected from the group consisting of anionic surfactants, nonionic surfactants, zwitterionic surfactants and an ethoxylated glycerol type compound and mixtures thereof; 0.05% to 5.0% of an acaricidal agent, 0.1% to 10% of a solubilizer, 0 to 1.0% of a perfume, essential oil or water insoluble hydrocarbon and the balance being water, wherein the composition does not contain a solid component having a mean particle size of 2 to 100 microns which would leave a pulverulent residue on the surface being treated or quartz, sand, siliceous earth, metal carbonate, $SiO_2$, amorphous silica, silicates, polyacrylates, xanthan gum.

According to the present invention, the role of the hydrocarbon can be provided by a non-water-soluble perfume. Typically, in aqueous based compositions the presence of a solubilizers, such as alkali metal lower alkyl aryl sulfonate hydrotrope, triethanolamine, urea, etc., is required for perfume dissolution, especially at perfume levels of 1% and higher, since perfumes are generally a mixture of fragrant essential oils and aromatic compounds which are generally not water-soluble. Therefore, by incorporating the perfume into the aqueous cleaning composition as the oil (hydrocarbon) phase of the ultimate o/w microemulsion composition, several different important advantages are achieved.

As used herein and in the appended claims the term "perfume" is used in its ordinary sense to refer to and include any non-water soluble fragrant substance or mixture of substances including natural (i.e., obtained by extraction of flower, herb, blossom or plant), artificial (i.e., mixture of natural oils or oil constituents) and synthetically produced substance) odoriferous substances. Typically, perfumes are complex mixtures of blends of various organic compounds such as alcohols, aldehydes, ethers, aromatic compounds and varying amounts of essential oils (e.g., terpenes) such as from 0% to 80%, usually from 10% to 70% by weight, the essential oils themselves being volatile odoriferous compounds and also serving to dissolve the other components of the perfume, wherein the solvent of the perfume which can be 50 to 70 wt. % of the perfume can exhibit acaricidal activity.

In the present invention the precise composition of the perfume is of no particular consequence to cleaning performance so long as it meets the criteria of water immiscibility and having a pleasing odor. Naturally, of course, especially for cleaning compositions intended for use in the home, the perfume, as well as all other ingredients, should be cosmetically acceptable, i.e., non-toxic, hypoallergenic, etc.. The instant compositions show a marked improvement in ecotoxocity as compared to existing commercial products.

The hydrocarbon such as a perfume is present in the all purpose cleaning, liquid crystal or microemulsion composition in an amount of from 0 to 10% by weight, preferably from 0.4% to 10% by weight, especially preferably from 0.5% to 5% by weight. If the amount of hydrocarbon (perfume) is less than 0.4% by weight it becomes more difficult to form the microemulsion. In the case of the liquid crystal one need at least 0.5 weight % of perfume, more preferably 1 weight %. If the hydrocarbon (perfume) is added in amounts more than 10% by weight, the cost is increased without any additional cleaning benefit and, in fact, with some diminishing of cleaning performance insofar as the total amount of greasy or oily soil which can be taken up in the oil phase of the microemulsion will decrease proportionately.

Furthermore, although superior grease removal performance will be achieved for perfume compositions not containing any terpene solvents, it is apparently difficult for perfumers to formulate sufficiently inexpensive perfume compositions for products of this type (i.e., very cost sensitive consumer-type products) which includes less than 20%, usually less than 30%, of such terpene solvents.

In place of the perfume one can employ an essential oil or a water insoluble paraffin or isoparaffin having 6 to 18 carbon or an essential oil.

The water-soluble organic surfactant materials which are used in forming the microemulsion all purpose cleaning, liquid crystal or light duty liquid cleaning compositions of this invention may be selected from the group consisting of water-soluble, non-soap, anionic surfactants, nonionic surfactants, zwitterionic surfactants and a partially esterified ethoxylated polyhydric alcohol such as a partially esterified ethoxylated glycerol and mixtures thereof.

Regarding the anionic surfactant present in the cleaning composition any of the conventionally used water-soluble anionic surfactants can be used in this invention. As used herein the term "anionic surfactant" is intended to refer to the class of anionic and mixed anionic-nonionic surfactants providing detersive action.

Suitable water-soluble non-soap, anionic surfactants include those surface-active or detergent compounds which contain an organic hydrophobic group containing generally 8 to 26 carbon atoms and preferably 10 to 18 carbon atoms in their molecular structure and at least one water-solubilizing group selected from the group of sulfonate, sulfate and carboxylate so as to form a water-soluble surfactant. Usually, the hydrophobic group will include or comprise a $C_8$–$C_{22}$ alkyl, alkyl or acyl group. Such surfactants are employed in the form of water-soluble salts and the salt-forming cation usually is selected from the group consisting of sodium, potassium, ammonium, magnesium and mono-, di- or tri-$C_2$–$C_3$ alkanolammonium, with the sodium, magnesium and ammonium cations again being preferred.

Examples of suitable sulfonated anionic surfactants are the well known higher alkyl mononuclear aromatic sulfonates such as the higher alkyl benzene sulfonates containing from 10 to 16 carbon atoms in the higher alkyl group in a straight or branched chain, $C_8$–$C_{15}$ alkyl toluene sulfonates and $C_8$–$C_{15}$ alkyl phenol sulfonates.

A preferred sulfonate is linear alkyl benzene sulfonate having a high content of 3- (or higher) phenyl isomers and a correspondingly low content (well below 50%) of 2- (or lower) phenyl isomers, that is, wherein the benzene ring is preferably attached in large part at the 3 or higher (for example, 4, 5, 6 or 7) position of the alkyl group and the content of the isomers in which the benzene ring is attached in the 2 or 1 position is correspondingly low. Particularly preferred materials are set forth in U.S. Pat. No. 3,320,174.

Other suitable anionic surfactants are the olefin sulfonates, including long-chain alkene sulfonates, long-chain hydroxyalkane sulfonates or mixtures of alkene sulfonates and hydroxyalkane sulfonates. These olefin sulfonate detergents may be prepared in a known manner by the reaction of sulfur trioxide ($SO_3$) with long-chain olefins containing 8 to 25, preferably 12 to 21 carbon atoms and having the formula $RCH{=}CHR_1$ where R is a higher alkyl group of 6 to 23 carbons and $R_1$ is an alkyl group of 1 to 17 carbons or hydrogen to form a mixture of sulfones and alkene sulfonic acids which is then treated to convert the sulfones to sulfonates. Preferred olefin sulfonates contain from 14 to 16 carbon atoms in the R alkyl group and are obtained by sulfonating an a-olefin.

Other examples of suitable anionic sulfonate surfactants are the paraffin sulfonates containing 10 to 20, preferably 13 to 17, carbon atoms. Primary paraffin sulfonates are made by reacting long-chain alpha olefins and bisulfites and paraffin sulfonates having the sulfonate group distributed along the paraffin chain are shown in U.S. Pat. Nos. 2,503,280; 2,507,088; 3,260,744; 3,372,188; and German Patent 735, 096.

Examples of satisfactory anionic sulfate surfactants are the $C_8$–$C_{18}$ alkyl sulfate salts and the ethoxylated $C_8$–$C_{18}$ alkyl ether sulfate salts having the formula $R(OC_2H_4)_n OSO_3M$ wherein n is 1 to 12, preferably 1 to 5, and M is a solubilizing cation selected from the group consisting of sodium, potassium, ammonium, magnesium and mono-, di- and triethanol ammonium ions. The alkyl sulfates may be obtained by sulfating the alcohols obtained by reducing glycerides of coconut oil or tallow or mixtures thereof and neutralizing the resultant product. On the other hand, the alkyl ether polyethenoxy sulfates are obtained by sulfating the condensation product of ethylene oxide with a $C_8$–$C_{18}$ alkanol and neutralizing the resultant product. The alkyl sulfates may be obtained by sulfating the alcohols obtained by reducing glycerides of coconut oil or tallow or mixtures thereof and neutralizing the resultant product. On the other hand, the alkyl ether polyethenoxy sulfates are obtained by sulfating the condensation product of ethylene oxide with a $C_8$–$C_{18}$ alkanol and neutralizing the resultant product. The alkyl ether polyethenoxy sulfates differ from one another in the number of moles of ethylene oxide reacted with one mole of alkanol. Preferred alkyl sulfates and preferred alkyl ether polyethenoxy sulfates contain 10 to 16 carbon atoms in the alkyl group.

The $C_8$–$C_{12}$ alkylphenyl ether polyethenoxy sulfates containing from 2 to 6 moles of ethylene oxide in the molecule also are suitable for use in the inventive compositions. These detergents can be prepared by reacting an alkyl phenol with 2 to 6 moles of ethylene oxide and sulfating and neutralizing the resultant ethoxylated alkylphenol.

Obviously, these anionic surfactants will be present either in acid form or salt form depending upon the pH of the final composition, with salt forming cation being the same as for the other anionic detergents.

Generally, the proportion of the nonsoap-anionic surfactant in the microemulsion, liquid crystal or all purpose cleaning composition will be in the range of 0 to 20.0 wt. %, preferably from 0.1% to 10%, by weight of the cleaning composition and 0 to 30 wt. %, more preferably 1 to 15 wt. % in the light duty liquid composition.

The nonionic surfactant can be present in the liquid cleaning composition is present in amounts of about 0 to 20%, preferably 1% to 18% by weight of the composition.

The water soluble nonionic surfactants which can be utilized in this invention are commercially well known and include the primary aliphatic alcohol ethoxylates, secondary aliphatic alcohol ethoxylates, alkylphenol ethoxylates and ethylene-oxide-propylene oxide condensates on primary alkanols, such a Plurafacs (BASF) and condensates of ethylene oxide with sorbitan fatty acid esters such as the Tweens (ICI). The nonionic synthetic organic detergents generally are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a water-soluble nonionic detergent. Further, the length of the polyethenoxy chain can be adjusted to achieve the desired balance between the hydrophobic and hydrophilic elements.

The nonionic detergent class includes the condensation products of a higher alcohol (e.g., an alkanol containing about 8 to 18 carbon atoms in a straight or branched chain configuration) condensed with about 5 to 30 moles of ethylene oxide, for example, lauryl or myristyl alcohol condensed with about 16 moles of ethylene oxide (EO), tridecanol condensed with about 6 to moles of EO, myristyl alcohol condensed with about 10 moles of EO per mole of myristyl alcohol, the condensation product of EO with a cut of coconut fatty alcohol containing a mixture of fatty alcohols with alkyl chains varying from 10 to about 14 carbon atoms in length and wherein the condensate contains either about 6 moles of EO per mole of total alcohol or about 9 moles of EO per mole of alcohol and tallow alcohol ethoxylates containing 6 EO to 11 EO per mole of alcohol.

A preferred group of the foregoing nonionic surfactants are the Neodol ethoxylates (Shell Co.), which are higher aliphatic, primary alcohol containing about 9–15 carbon atoms, such as $C_9$–$C_{11}$ alkanol condensed with 8 moles of ethylene oxide (Neodol 91-8), $C_{12\text{-}13}$ alkanol condensed with 6.5 moles ethylene oxide (Neodol 23-6.5), $C_{12\text{-}15}$ alkanol condensed with 12 moles ethylene oxide (Neodol 25-12), $C_{14\text{-}15}$ alkanol condensed with 13 moles ethylene oxide (Neodol 45-13), and the like. Such ethoxamers have an HLB (hydrophobic lipophilic balance) value of about 8–15 and give good ONV emulsification, whereas ethoxamers with HLB values below 8 contain less than 5 ethyleneoxide groups and tend to be poor emulsifiers and poor detergents.

Additional satisfactory water soluble alcohol ethylene oxide condensates are the condensation products of a secondary aliphatic alcohol containing 8 to 18 carbon atoms in a straight or branched chain configuration condensed with 5 to 30 moles of ethylene oxide. Examples of commercially available nonionic detergents of the foregoing type are $C_{11}$–$C_{15}$ secondary alkanol condensed with either 9 EO (Tergitol 15-S-9) or 12 EO (Tergitol 15-S-12) marketed by Union Carbide.

Other suitable nonionic detergents include the polyethylene oxide condensates of one mole of alkyl phenol containing from about 8 to 18 carbon atoms in a straight- or branched chain alkyl group with about 5 to 30 moles of ethylene oxide. Specific examples of alkyl phenol ethoxylates include nonyl phenol condensed with about 9.5 moles of EO per mole of nonyl phenol, dinonyl phenol condensed with about 12 moles of EO per mole of dinonyl phenol, dinonyl phenol condensed with about 15 moles of EO per mole of phenol and di-isoctylphenol condensed with about 15 moles of EO per mole of phenol. Commercially available nonionic surfactants of this type include Igepal CO-630 (nonyl phenol ethoxylate) marketed by GAF Corporation.

Condensates of 2 to 30 moles of ethylene oxide with sorbitan mono- and tri-$C_{10}$–$C_{20}$ alkanoic acid esters having a HLB of 8 to 15 also may be employed as the nonionic detergent ingredient in the described shampoo. These surfactants are well known and are available from Imperial Chemical Industries under the Tween trade name. Suitable surfactants include polyoxyethylene (4) sorbitan monolaurate, polyoxyethylene (4) sorbitan monostearate, polyoxyethylene (20) sorbitan trioleate and polyoxyethylene (20) sorbitan tristearate.

The instant composition can contain a composition (herein after referred to as ethoxylated glycerol type compound) which is a mixture of a fully esterified ethoxylated polyhydric alcohol, a partially esterified ethoxylated polyhydric alcohol and a nonesterified ethoxylated polyhydric alcohol, wherein the preferred polyhydric alcohol is glycerol, and the compound is

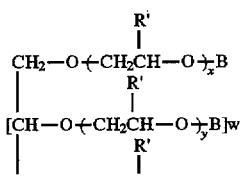   Formula (I)

and

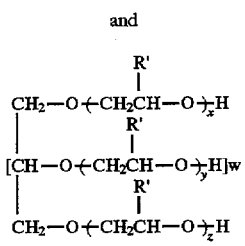   Formula (II)

wherein w equals one to four, most preferably one. B is selected from the group consisting of hydrogen or a group represented by:

wherein R is selected from the group consisting of alkyl group having 6 to 22 carbon atoms, more preferably 11 to 15 carbon atoms and alkenyl groups having 6 to 22 carbon atoms, more preferably 11 to 15 carbon atoms, wherein a hydrogenated tallow alkyl chain or a coco alkyl chain is most preferred, wherein at least one of the B groups is represented by said

and R' is selected from the group consisting of hydrogen and methyl groups; x, y and z have a value between 0 and 60, more preferably 0 to 40, provided that (x+y+z) equals 2 to 100, preferably 4 to 24 and most preferably 4 to 19, wherein in Formula (I) the wt. ratio of monoester/diester/triester is 45 to 90/5 to 40/1 to 20, more preferably 50 to 90/9 to 32/1 to 12, wherein the wt. ratio of Formula (I) to Formula (II) is a value between 3 to 0.02, preferably 3 to 0.1, most preferably 1.5 to 0.2, wherein it is most preferred that there is more of Formula (II) than Formula (I) in the mixture that forms the compound.

The ethoxylated glycerol type compound used in the instant composition is manufactured by the Kao Corporation and sold under the trade name Levenol such as Levenol F-200 which has an average EO of 6 and a molar ratio of coco fatty acid to glycerol of 0.55 or Levenol V501/2 which has an average EO of 17 and a molar ratio of tallow fatty acid to glycerol of 1.0. It is preferred that the molar ratio of the fatty acid to glycerol is less than 1.7, more preferably less than 1.5 and most preferably less than 1.0. The ethoxylated glycerol type compound has a molecular weight of 400 to 1600, and a pH (50 grams/liter of water) of 5–7. The Levenol compounds are substantially non irritant to human skin and have a primary biodegradabillity higher than 90% as measured by the Wickbold method Bias-7d.

Two examples of the Levenol compounds are Levenol V-501/2 which has 17 ethoxylated groups and is derived from tallow fatty acid with a fatty acid to glycerol ratio of 1.0 and a molecular weight of 1465 and Levenol F-200 has 6 ethoxylated groups and is derived from coco fatty acid with a fatty acid to glycerol ratio of 0.55. Both Levenol F-200 and Levenol V-501/2 are composed of a mixture of Formula (I) and Formula (II). The Levenol compounds has ecoxicity values of algae growth inhibition >100 mg/liter; acute toxicity for Daphniae >100 mg/liter and acute fish toxicity >100 mg/liter. The Levenol compounds have a ready biodegradability higher than 60% which is the minimum required value according to OECD 301B measurement to be acceptably biodegradable.

Polyesterified nonionic compounds also useful in the instant compositions are Crovol PK-40 and Crovol PK-70 manufactured by Croda GMBH of the Netherlands. Crovol PK-40 is a polyoxyethylene (12) Palm Kernel Glyceride which has 12 EO groups. Crovol PK-70 which is preferred is a polyoxyethylene (45) Palm Kernel Glyceride have 45 EO groups.

In the dilute o/w microemulsion compositions or liquid crystal compositions the ethoxylated glycerol type compounds or the polyesterified nonionic compounds will be present in admixture with the anionic detergent. The proportion of the ethoxylated glycerol type compound or the polyesterified nonionic solubilizing agent based upon the weight of the liquid crystal composition all purpose cleaning composition, light duty liquid composition or the microemulsion composition will be 0.1 to 20%, more preferably 0.7% to 15%, most preferably 0.8% to 10% by weight.

The cosurfactant may play an essential role in the formation of the the liquid crystal composition or dilute o/w microemulsion and the concentrated microemulsion compositions and can function as a solubilizing agent in the light duty liquid composition. Highly suitable cosurfactants for the microemulsion over temperature ranges extending from 5° C. to 43° C. are water-soluble $C_3$–$C_4$ alkanols, polypropylene glycol of the formula $HO(CH_3CHCH_2O)_nH$ wherein n is a number from 2 to 18 and monoalkyl ethers and esters of ethylene glycol and propylene glycol having the structural formulas $R(X)_nOH$ and $R_1(X)_nOH$ wherein R is $C_1$–C6 alkyl, $R_1$ is $C_2$–$C_4$ acyl group, X is $(OCH_2CH_2)$ or $(OCH_2(CH_3)CH)$ and n is a number from 1 to 4.

Methanol and ethanol are explicitly excluded from the instant composition because of their low flash point.

Representative members of the polypropylene glycol include dipropylene glycol and polypropylene glycol having a molecular weight of 200 to 1000, e.g., polypropylene glycol 400. Other satisfactory glycol ethers are ethylene glycol monobutyl ether (butyl cellosolve), diethylene glycol monobutyl ether (butyl carbitol), triethylene glycol monobutyl ether, mono, di, tri propylene glycol monobutyl ether, tetraethylene glycol monobutyl ether, propylene glycol tertiary butyl ether, ethylene glycol monoacetate and dipropylene glycol propionate. When these glycol type cosurfactants are at a concentration of at least 1.0 weight %, more preferably at least 2.0 weight % in combination with a perfume at a concentration of at least 0.5 weight %, more preferably 1.5 weight % one can form a liquid crystal composition.

The amount of cosurfactant required to stabilize the liquid crystal compositions or the microemulsion compositions will, of course, depend on such factors as the surface tension characteristics of the cosurfactant, the type and amounts of the primary surfactants and perfumes, and the type and amounts of any other additional ingredients which may be present in the composition and which have an influence on the thermodynamic factors enumerated above. Generally, amounts of cosurfactant in the range of from 0% to 20%, preferably from 0.5% to 15%, especially preferably from 1% to 10%, by weight provide stable dilute o/w microemulsions for the above-described levels of primary surfactants and perfume and any other additional ingredients as described below.

The water-soluble zwitterionic surfactant, which can be an ingredient of present liquid detergent composition, constitutes about 0 to 10%, more preferably 0.1 to 8%, by weight and provides good foaming properties and mildness to the present nonionic based liquid detergent. The zwitterionic surfactant is a water-soluble betaine having the general formula:

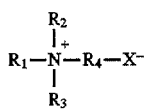

wherein $X^-$ is selected from the group consisting of $CO_2^-$ and $SO_3^-$ and $R_1$ is an alkyl group having 10 to about 20 carbon atoms, preferably 12 to 16 carbon atoms, or the amido radical:

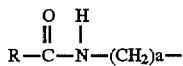

wherein R is an alkyl group having about 9 to 19 carbon atoms and a is the integer 1 to 4; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyldimethyl betaines include decyl dimethyl betaine or 2-(N-decyl-N, N-dimethyl-ammonia) acetate, coco dimethyl betaine or 2-(N-coco N,N-dimethylammonia) acetate, myristyl dimethyl betaine, plamityl dimethyl betaine, lauryl dimethyl betaine, cetyl dimethyl betaine, stearyl dimethyl betaine, etc. The amidobetaines similarly include cocoamidoethylbetaine, cocoamidopropyl betaine and the like. A preferred betaine is coco ($C_8$–$C_{18}$) amidopropyl dimethyl betaine. Two preferred betaine surfactants are Rewoteric AMB 13 and Golmschmidt Betaine L7.

The essential ingredients discussed above in forming the light duty liquid composition can be solubilized in one preferred embodiment of the invention in an aqueous medium comprising water an alkyl monoethanol amides such as $C_{12}$–$C_{14}$ alkyl monoethanol amide (LMMEA) at a concentration of 1 to 4 wt. %, and/or an alkyl diethanol amides such as coco diethanol amide (CDEA) or lauryl diethanol amide (LDEA) at a concentration of 1 to 4 wt. %.

Less preferred solubilizing agents are $C_2$–$C_3$ mono and di-hydroxy alkanols, e.g., ethanol, isopropanol and propylene glycol. Suitable water soluble hydrotropic salts include sodium, potassium, ammonium and mono-, di- and triethanolammonium salts. While the aqueous medium is primarily water, preferably said solubilizing agents are included in order to control the viscosity of the liquid composition and to control low temperature cloud clear properties. Usually, it is desirable to maintain clarity to a temperature in the range of 5° C. to 10° C. Therefore, the proportion of solubilizer generally will be from about 0.1% to 10%, most preferably 3%–8%, by weight of the detergent composition with the proportion of ethanol, when present, being 5% of weight or less in order to provide a composition having a flash point above about 46° C. Preferably the solubilizing ingredient will be a mixture of ethanol and a water soluble salt of a $C_1$–$C_3$ substituted benzene sulfonate hydrotrope such as sodium xylene sulfonate or sodium cumene sulfonate or a mixture of said sulfonates or ethanol and urea. Inorganic alkali metal or alkaline earth metal salts such as sodium sulfate, magnesium sulfate, sodium chloride and sodium citrate can be added at concentrations of 0.5 to 4.0 wt.% to modify the cloud point of the nonionic surfactant and thereby control the haze of the resultant solution. Various other ingredients such as urea at a concentration of about 0.5 to 4.0 wt.% or urea at the same concentration in combination with ethanol at a concentration of about 0.5 to 4.0 wt.% can be used as solubilizing agents. Other ingredients which have been added to the compositions at concentrations of about 0.1 to 4.0 wt. percent are perfumes, preservatives, color stabilizers, sodium bisulfite, ETDA, and proteins such as lexine protein. One to 4 wt. % of an alkali metal salt of isethionic acid having the formula $CH_2OHCHSO_3H$ can be used in the amide free formula of the instant composition as a substitute for the amide as a solubilizing agent.

The foregoing solubilizing ingredients also facilitate the manufacture of the light duty liquid compositions because they tend to inhibit gel formation.

In addition to the previously mentioned essential and optional constituents of the light duty liquid detergent, one may also employ normal and conventional adjuvants, provided they do not adversely affect the properties of the detergent. Thus, there may be used various coloring agents and perfumes; sequestering agents such as ethylene diamine tetraacetates; magnesium sulfate heptahydrate; pearlescing agents and opacifiers; pH modifiers; etc. The proportion of such adjuvant materials, in total will normally not exceed 15% of weight of the detergent composition, and the percentages of most of such individual components will be about 0.1 to 5% by weight and preferably less than about 2% by weight. Sodium bisulfite can be used as a color stabilizer at a concentration of about 0.01 to 0.2 wt.%. Typical perservatives are dibromodicyano-butane, citric acid, benzylic alcohol and poly (hexamethylene-biguamide) hydrochloride and mixtures thereof.

The instant light duty liquid compositions can contain about 0 to about 15 wt. %, more preferably 0.1 to 15 wt. % of an alkyl polysaccharide surfactant. The alkyl polysaccharides surfactants, which are used in conjunction with the aforementioned surfactant have a hydrophobic group containing from about 8 to about 20 carbon atoms, preferably from about 10 to about 16 carbon atoms, most preferably from about 12 to about 14 carbon atoms, and polysaccharide hydrophilic group containing from about 1.5 to about 10, preferably from about 1.5 to about 4, most preferably from about 1.6 to about 2.7 saccharide units (e.g., galactoside, glucoside, fructoside, glucosyl, fructosyl; and/or galactosyl units). Mixtures of saccharide moieties may be used in the alkyl polysaccharide surfactants. The number x indicates the number of saccharide units in a particular alkyl polysaccharide surfactant. For a particular alkyl polysaccharide molecule x can only assume integral values. In any physical sample of alkyl polysaccharide surfactants there will be in general molecules having different x values. The physical sample can be characterized by the average value of x and this average value can assume non-integral values. In this specification the values of x are to be understood to be average values. The hydrophobic group (R) can be attached at the 2- , 3-, or 4- positions rather than at the 1-position, (thus giving e.g. a glucosyl or galactosyl as opposed to a glucoside or galactoside). However, attachment through the 1- position, i.e., glucosides, galactoside, fructosides, etc., is preferred. In the preferred product the additional saccharide units are predominately attached to the previous saccharide unit's 2-position. Attachment through the 3-, 4-, and 6- positions can also occur. Optionally and less desirably there can be a polyalkoxide chain joining the hydrophobic moiety (R) and the polysaccharide chain. The preferred alkoxide moiety is ethoxide.

Typical hydrophobic groups include alkyl groups, either saturated or unsaturated, branched or unbranched containing from about 8 to about 20, preferably from about 10 to about 18 carbon atoms. Preferably, the alkyl group is a straight chain saturated alkyl group. The alkyl group can contain up to 3 hydroxy groups and/or the polyalkoxide chain can contain up to about 30, preferably less than about 10, alkoxide moieties.

Suitable alkyl polysaccharides are decyl, dodecyl, tetradecyl, pentadecyl, hexadecyl, and octadecyl, di-, tri-, tetra-, penta-, and hexaglucosides, galactosides, lactosides, fructosides, fructosyls, lactosyls, glucosyls and/or galactosyls and mixtures thereof.

The alkyl monosaccharides are relatively less soluble in water than the higher alkyl polysaccharides. When used in admixture with alkyl polysaccharides, the alkyl monosaccharides are solubilized to some extent. The use of alkyl monosaccharides in admixture with alkyl polysaccharides is a preferred mode of carrying out the invention. Suitable mixtures include coconut alkyl, di-, tri-, tetra-, and pentaglucosides and tallow alkyl tetra-, penta-, and hexaglucosides.

The preferred alkyl polysaccharides are alkyl polyglucosides having the formula

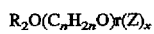

wherein Z is derived from glucose, R is a hydrophobic group selected from the group consisting of alkyl, alkylphenyl, hydroxyalkylphenyl, and mixtures thereof in which said alkyl groups contain from about 10 to about 18, preferably from about 12 to about 14 carbon atoms; n is 2 or 3 preferably 2, r is from 0 to 10, preferable 0; and x is from 1.5 to 8, preferably from 1.5 to 4, most preferably from 1.6 to 2.7. To prepare these compounds a long chain alcohol ($R_2OH$) can be reacted with glucose, in the presence of an acid catalyst to form the desired glucoside. Alternatively the alkyl polyglucosides can be prepared by a two step procedure in which a short chain alcohol ($R_1OH$) can be reacted with glucose, in the presence of an acid catalyst to form the desired glucoside. Alternatively the alkyl polyglucosides can be prepared by a two step procedure in which a short chain alcohol ($C_{1-6}$) is reacted with glucose or a polyglucoside (x=2 to 4) to yield a short chain alkyl glucoside (x=1 to 4) which can in turn be reacted with a longer chain alcohol ($R_2OH$) to displace the short chain alcohol and obtain the desired alkyl polyglucoside. If this two step procedure is used, the short chain alkylglucosde content of the final alkyl polyglucoside material should be less than 50%, preferably less than 10%, more preferably less than about 5%, most preferably 0 of the alkyl polyglucoside.

The amount of unreacted alcohol (the free fatty alcohol content) in the desired alkyl polysaccharide surfactant is preferably less than about 2%, more preferably less than about 0.5% by weight of the total of the alkyl polysaccharide. For some uses it is desirable to have the alkyl monosaccharide content less than about 10%.

The used herein, "alkyl polysaccharide surfactant" is intended to represent both the preferred glucose and galactose derived surfactants and the less preferred alkyl polysaccharide surfactants. Throughout this specification, "alkyl polyglucoside" is used to include alkyl polyglycosides because the stereochemistry of the saccharide moiety is changed during the preparation reaction.

An especially preferred APG glycoside surfactant is APG 625 glycoside manufactured by the Henkel Corporation of Ambler, Pa. APG25 is a nonionic alkyl polyglycoside characterized by the formula:

wherein n=10 (2%); n=122 (65%); n=14 (21–28%); n=16 (4–8%) and n=18 (0.5%) and x (degree of polymerization) =1.6. APG 625 has: a pH of 6 to 10 (10% of APG 625 in distilled water); a specific gravity at 25° C. of 1.1 g/ml; a density at 25° C. of 9.1 lbs/gallon; a calculated HLB of 12.1 and a Brookfield viscosity at 35° C., 21 spindle, 5–10 RPM of 3,000 to 7,000 cps.

The acaricidal agent is used in the light duty liquid composition, microemulsion composition, liquid crystal composition or all purpose hard surface cleaning composition at a concentration of about 0.05 to 5.0 wt. %, more preferably 0.075 to 3 wt. %. The acaricidal agent is selected from the group consisting of

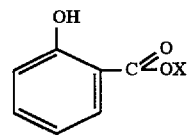

wherein

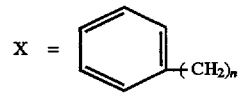

or a $C_6$–$C_{14}$ alkyl group, wherein n equals 1 to 3;

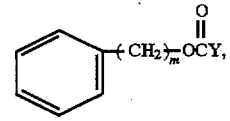

wherein m=1 to 3 and x is a C1 to C6 alkyl group,

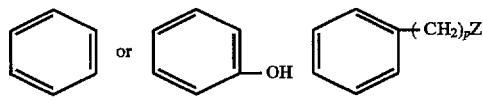

wherein p=1 to 3 and Z is a

group; carvone; citral limarome; 50 wt. thymol in benzyl benzoate; alpha pinene; citronellol dextro;hedione; linalool citronella; eucalyptus globulux; thyme white; lavandin oil grosso; a $C_6$ to $C_{14}$ aldehyde such as methyl nonyl aldehyde, hexylcinnamic aldehyde; litsea cubebaoil; 50 wt. % camphor white in benzyl benzoate; terpenolene; rosemary oil. terpineol and verdox; 50 wt. % of menthol in benzyl benzoate. Especially preferred acaricidal agents are benzyl benzoate, benzyl alcohol; phenyl ethyl benzoate, benzaldehyde, carvone, methyl salicylate, citral lemarome, 50 wt. % of thymol in benzyl benzoate, 50 wt. % of camphor white in benzyl benzoate and 50 wt. % of menthol in benzyl benzoate.

The ability to formulate neutral products without builders which have grease removal and mite killing capacities is a feature of the present invention because the prior art microemulsion formulations most usually are highly alkaline or highly built or both.

The final essential ingredient in the inventive hard surface cleaning, light duty liquid, liquid crystal or microemulsion compositions having improved interfacial tension properties is water which is the balance of the composition.

As believed to have been made clear from the foregoing description, the dilute microemulsion liquid all-purpose cleaning or liquid crystal compositions of this invention are especially effective when used as is, that is, without further dilution in water, since the properties of the composition as an o/w microemulsion are best manifested in the neat (undiluted) form. However, at the same time it should be understood that depending on the levels of surfactants, cosurfactants, perfume and other ingredients, some degree of dilution without disrupting the microemulsion, per se, is possible. For example, at the preferred low levels of active surfactant compounds (i.e., primary anionic and nonionic surfactants) dilutions up to 50% will generally be well tolerated without causing phase separation, that is, the microemulsion state will be maintained.

However, even when diluted to a great extent, such as a 2- to 10-fold or more dilution, for example, the resulting compositions are still effective in cleaning greasy, oily and other types of soil. Furthermore, the presence of magnesium ions or other polyvalent ions, e.g., aluminum, as will be described in greater detail below further serves to boost cleaning performance of the primary detergents in dilute usage.

On the other hand, it is also within the scope of this invention to formulate highly concentrated microemulsions which will be diluted with additional water before use.

The present invention also relates to a stable concentrated microemulsion composition comprising approximately by weight:

(a) 1 to 30% of an anionic surfactant;

(b) 0.6 to 20% of a nonionic surfactant or an ethoxylated glycerol type compound;

(c) 2 to 30% of a cosurfactant;

(d) 0.4 to 10% of a water insoluble hydrocarbon or perfume;

(e) 0.05 to 5.0% of an acaricidal agent;

(f) 0 to 15% of magnesium sulfate heptahydrate; and (g) the balance being water, wherein the composition does not contain a solid component having a mean particle size of 2 to 100 which would leave a pulverulent residue on the surface being treated or quartz, sand, siliceous earth, metal carbonate, $SiO_2$, amorphous silica, silicates, polyacrylates, xanthan gum.

The present invention also relates to a stable liquid crystal microemulsion comprising approximately by weight:

(a) 0 to 20% of an anionic surfactant;

(b) 0.1 to 20% of a nonionic surfactant or an ethoxylated glycerol type compound;

(c) 0 to 2.5% of a fatty acid;

(d) 1 to 20% of a cosurfactant;

(e) 0.5 to 10% of a water insoluble hydrocarbon, essential oil or perfume;

(f) 0 to 15% of magnesium sulfate heptahydrate;

(g) 0.05 to 5.0% of an acaricidal agent; and (h) the balance being water, wherein the composition does not contain a solid component having a mean particle size of 2 to 100 which would leave a pulverulent residue on the surface being treated or quartz, sand, siliceous earth, metal carbonate, $SiO_2$, amorphous silica, silicates, polyacrylates, xanthan gum.

Such concentrated microemulsions can be diluted by mixing with up to 20 times or more, preferably 4 to 10 times their weight of water to form o/w microemulsions similar to the diluted microemulsion compositions described above. While the degree of dilution is suitably chosen to yield an o/w microemulsion composition after dilution, it should be recognized that during the course of dilution both microemulsion and non-microemulsions may be successively encountered.

In addition to the above-described essential ingredients required for the formation of the liquid crystal composition, all purpose hard surface cleaning composition or the microemulsion composition, the compositions of this invention may often and preferably do contain one or more additional ingredients which serve to improve overall product performance.

One such ingredient is an inorganic or organic salt of oxide of a multivalent metal cation, particularly $Mg^{++}$. The metal salt or oxide provides several benefits including improved cleaning performance in dilute usage, particularly in soft water areas, and minimized amounts of perfume required to obtain the microemulsion state. Magnesium sulfate, either anhydrous or hydrated (e.g., heptahydrate), is especially preferred as the magnesium salt. Good results also have been obtained with magnesium oxide, magnesium chloride, magnesium acetate, magnesium propionate and magnesium hydroxide. These magnesium salts can be used with formulations at neutral or acidic pH since magnesium hydroxide will not precipitate at these pH levels.

Although magnesium is the preferred multivalent metal from which the salts (inclusive of the oxide and hydroxide) are formed, other polyvalent metal ions also can be used provided that their salts are nontoxic and are soluble in the aqueous phase of the system at the desired pH level. Thus, depending on such factors as the pH of the system, the nature of the primary surfactants and cosurfactant, and so on, as well as the availability and cost factors, other suitable polyvalent metal ions include aluminum, copper, nickel, iron, calcium, etc. It should be noted, for example, that with the preferred paraffin sulfonate anionic detergent calcium salts will precipitate and should not be used. It has also been found that the aluminum salts work best at pH below 5 or when a low level, for example 1 weight percent, of citric acid is added to the composition which is designed to have a neutral pH. Alternatively, the aluminum salt can be directly added as the citrate in such case. As the salt, the same general classes of anions as mentioned for the magnesium salts can be used, such as halide (e.g., bromide, chloride), sulfate, nitrate, hydroxide, oxide, acetate, propionate, etc.

Preferably, in the dilute compositions the metal compound is added to the composition in an amount sufficient to provide at least a stoichiometric equivalence between the anionic surfactant and the multivalent metal cation. For example, for each gram-ion of Mg++ there will be 2 gram moles of paraffin sulfonate, alkylbenzene sulfonate, etc., while for each gram-ion of $Al^{3+}$ there will be 3 gram moles of anionic surfactant. Thus, the proportion of the multivalent salt generally will be selected so that one equivalent of compound will neutralize from 0.1 to 1.5 equivalents, preferably 0.9 to 1.4 equivalents, of the acid form of the anionic surfactant.

At higher concentrations of anionic surfactant, the amount of multivalent salt will be in range of 0.5 to 1 equivalents per equivalent of anionic surfactant.

The liquid crystal composition or the o/w microemulsion compositions will include from 0% to 2.5%, preferably from 0.1% to 2.0% by weight of the composition of a $C8-C_{22}$ fatty acid or fatty acid soap as a foam suppressant. The addition of fatty acid or fatty acid soap provides an improvement in the rinseability of the composition whether applied in neat or diluted form. Generally, however, it is necessary to increase the level of cosurfactant to maintain product stability when the fatty acid or soap is present. If more than 2.5wt % of the fatty acid is used in the instant compositions, the composition will become unstable at low temperatures as well as having an objectionable smell.

As example of the fatty acids which can be used as such or in the form of soap, mention can be made of distilled coconut oil fatty acids, "mixed vegetable" type fatty acids (e.g. high percent of saturated, mono-and/or polyunsaturated $C_{18}$ chains); oleic acid, stearic acid, palmitic acid, eiocosanoic acid, and the like, generally those fatty acids having from 8 to 22 carbon atoms being acceptable.

The all-purpose hard surface cleaning composition, liquid crystal or microemulsion composition of this invention may, if desired, also contain other components either to provide additional effect or to make the product more attractive to the consumer. The following are mentioned by way of example: Colors or dyes in amounts up to 0.5% by weight; bactericides in amounts up to 1% by weight; perservatives or antioxidizing agents, such as formalin, 5-bromo-5-nitrodioxan-1,3; 5-chloro-2-methyl-4-isothaliazolin-3-one, 2,6-di-tert.butyl-p-cresol, etc., in amounts up to 2% by weight; and pH adjusting agents, such as sulfuric acid or sodium hydroxide, as needed. Furthermore, if opaque compositions are desired, up to 4% by weight of an opacifier may be added.

In final form, the all-purpose liquids are clear oil-in-water microemulsions or liquid crystal compositions and exhibit stability at reduced and increased temperatures. More specifically, such compositions remain clear and stable in the range of 5° C. to 50° C., especially 10° C. to 43° C. Such compositions exhibit a pH in the acid or neutral range depending on intended end use. The liquid microemulsion compositions are readily pourable and exhibit a viscosity in the range of 6 to 60 milliPascal. second (mPas.) as measured at 25° C. with a Brookfield RVT Viscometer using a #1 spindle rotating at 20 RPM. Preferably, the viscosity is maintained in the range of 10 to 40 mPas.

The compositions are directly ready for use or can be diluted as desired and in either case no or only minimal rinsing is required and substantially no residue or streaks are left behind. Furthermore, because the compositions are free of detergent builders such as alkali metal polyphosphates they are environmentally acceptable and provide a better "shine" on cleaned hard surfaces.

When intended for use in the neat form, the liquid compositions can be packaged under pressure in an aerosol container or in a pump-type sprayer for the so-called spray-and-wipe type of application.

Because the compositions as prepared are aqueous liquid formulations and since no particular mixing is required to form the microemulsion composition, liquid crystal composition or all purpose hard surface composition, the compositions are easily prepared simply by combining all the ingredients in a suitable vessel or container. The order of mixing the ingredients is not particularly important and generally the various ingredients can be added sequentially or all at once or in the form of aqueous solutions of each or all of the primary detergents and cosurfactants can be separately prepared and combined with each other and with the perfume. The magnesium salt, or other multivalent metal compound, when present, can be added as an aqueous solution thereof or can be added directly. It is not necessary to use elevated temperatures in the formation step and room temperature is sufficient.

The instant microemulsion formulas explicitly exclude alkali metal silicates and alkali meta builders such as alkali metal polyphosphates, alkali metal carbonates, alkali metal phosphonates and alkali metal citrates because these materials, if used in the instant composition, would cause the composition to have a high pH as well as leaving residue on the surface being cleaned.

It is contemplated within the scope of the instant invention that the ethoxylated glycerol type compound can be employed in hard surface cleaning compositions such as wood cleaners, window cleaners and light duty liquid cleaners, wherein improvements in a grease release effect in desirable.

The following examples illustrate liquid cleaning compositions of the described invention. Unless otherwise specified, all percentages are by weight. The exemplified compositions are illustrative only and do not limit the scope of the invention. Unless otherwise specified, the proportions in the examples and elsewhere in the specification are by weight.

EXAMPLE 1

The following compositions in wt. % were prepared at 25° C. by simple mixing:

| | A | B | C | D | E | F | G |
|---|---|---|---|---|---|---|---|
| Ethoxylated nonionic surfactant | | | | | | | 2.3 |
| Levenol F-200 | 2.3 | 2.3 | 2.3 | 2.3 | 2.3 | 2.3 | |
| Sodium $C_{13}$-$C_{17}$ paraffin sulfonate | 4.7 | 4.7 | 4.7 | 4.7 | 4.7 | 4.7 | 4.7 |
| Diethylene glycol monobutyl ether | 4.0 | 4.0 | 4.0 | 4.0 | 4.0 | 4.0 | 4.0 |
| Fatty acid | 0.75 | 0.75 | 0.75 | 0.75 | 0.75 | 0.75 | 0.75 |
| MgSO4 7 H2O | 2.2 | 2.2 | 2.2 | 2.2 | 2.2 | 2.2 | 2.2 |
| Perfume | 0.8 | 0.8 | 0.8 | 0.8 | 0.8 | 0.8 | 0.8 |
| Water | Bal | Bal | Bal | Bal | Bal | Bal | Bal |
| Benzyl benzoate | 0.3 | 0.5 | | | | | |
| Phenylethyl benzoate | | | 0.3 | | | | |
| Phenylethyl alcohol | | | | 0.3 | | | |
| Benzyl aldehyde | | | | | 0.3 | | |
| Grams APC/100 ml water | 10 | 1.5 | 10 | 100 | 10 | 1.5 | 1.5 |
| Contact time minutes | 30 | 15 | 30 | 30 | 30 | 15 | 15 |
| % dead mites | 89 | 100 | 78 | 88 | 87 | 12 | 10 |

The acaricidal test for mites is done in liquid medium in 24 wells plastic plates. About 30 living mites are placed in the well with the nourishing culture medium and then covered with either water (background values) or the APC diluted (or any other liquid product to be tested) in water and left in contact for various contact times. The remaining living mites are counted by observation under the microscope after the envisaged contact time. APC dilutions in water can be from 1.5% to 50% and neat usage is also tested. Contact times with mites can be 5 minutes up to 3 hours.

What is claimed is:

1. A microemulsion cleaning composition comprising:

(a) 0.1 wt. % to 20 wt. % of an ethoxylated nonionic surfactant or mixture of

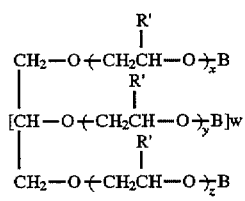 (I)

and

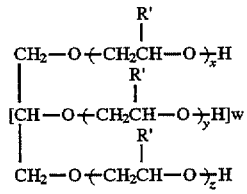 (II)

wherein w equals one to four; B is selected from the group consisting of hydrogen and a group represented by:

wherein R is selected from the group consisting of alkyl group having 6 to 22 carbon atoms, and alkenyl groups having 6 to 22 carbon atoms, wherein at least one of the B groups is represented by said

R' is selected from the group consisting of hydrogen and methyl groups; x, y and z have a value between 0 and 60, provided that (x+y+z) equals 2 to 100, wherein in Formula (I) the weight ratio of monoester/diester/triester is 45 to 90/5 to 40/1 to 20, wherein the weight ratio of Formula (I) to Formula (II) is a value between 3 and 0.02;

(b) 0 wt. % to 20 wt. % of an anionic surfactant, wherein the anionic surfactant is selected from the group consisting of sulfonate and sulfate surfactants;

(c) 0.1 wt. % to 20 wt. % of a glycol ether or a $C_3$–$C_6$ aliphatic carboxylic acid cosurfactant;

(d) 0.4 wt. % to 10 wt. % of a water insoluble hydrocarbon, essential oil or a perfume;

(e) 0.05 wt. % to 5.0 wt. % of an acaricidal agent selected from the group consisting of:

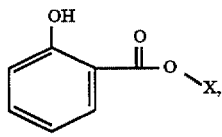

wherein

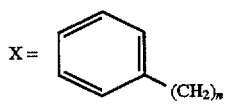

or a $C_6$–$C_{14}$ alkyl group, wherein n=1 to 3;

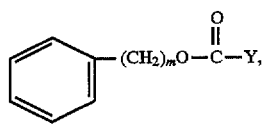

wherein m=1 to 3 and Y is a $C_1$–$C_6$ alkyl group,

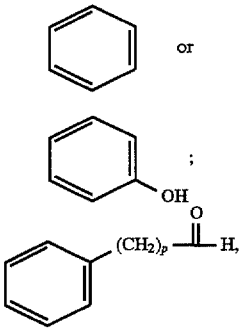

wherein p=1 to 3; carvone; and (f) the balance being water, wherein the composition does not contain a solid component having a mean particle size of 2 to 100 microns and wherein 50 to 70 wt. % of the essential oil or perfume may exhibit acaricidal activity.

2. The cleaning composition of claim 1 which further contains a salt of a multivalent metal cation in an amount sufficient to provide from 0.5 to 1.5 equivalents of said cation per equivalent of said anionic surfactant.

3. The cleaning composition of claim 2 wherein the multivalent metal cation is magnesium or aluminium.

4. The cleaning composition of claim 2, wherein said composition contains 0.9 to 1.4 equivalents of said cation per equivalent of anionic surfactant.

5. The cleaning composition of claim 2 wherein said salt is magnesium oxide, magnesium chloride or magnesium sulfate.

6. The cleaning composition of claim 1 further including a fatty acid which has 8 to 22 carbon atoms.

7. The cleaning composition of claim 1 wherein the cosurfactant is a water soluble glycol ether.

8. The cleaning composition of claim 7 wherein the glycol ether is selected from the group consisting of ethylene glycol monobutyl ether, diethylene glycol monobutyl ether, triethylene glycol monobutyl ether, and propylene glycol tert.butyl ether, mono-, di- and tri-propylene glycol monobutyl ether.

9. The cleaning composition of claim 8 wherein the glycol ether is ethylene glycol monobutyl ether or diethylene glycol monobutyl ether.

10. The cleaning composition of claim 1 wherein the anionic surfactant is a $C_9$–$C_{15}$ alkyl benzene sulfonate or a $C_{10}$–$C_{20}$ alkane sulfonate.

11. A stable concentrated microemulsion composition comprising approximately by weight:

(a) 1 to 30% of an anionic surfactant, wherein the anionic surfactant is selected from the group consisting of sulfonate and sulfate surfactants;

(b) 0.5 to 20% of an ethoxylated nonionic surfactant or a mixture of

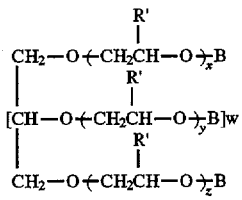 (I)

and

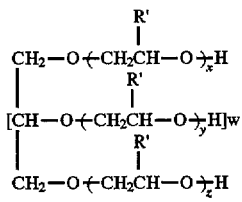 (II)

wherein w equals one to four; B is selected from the group consisting of hydrogen and a group represented by:

wherein R is selected from the group consisting of alkyl group having 6 to 22 carbon atoms, and alkenyl groups having 6 to 22 carbon atoms, wherein at least one of the B groups is represented by said

R' is selected from the group consisting of hydrogen and methyl groups; x, y and z have a value between 0 and 60, provided that (x+y+z) equals 2 to 100, wherein in Formula (I) the weight ratio of monoester/diester/triester is 45 to 90/5 to 40/1 to 20, wherein the weight ratio of Formula (I) to Formula (II) is a value between 3 and 0.02;

(c) 2 to 30% of a glycol ether or a $C_3$–$C_6$ aliphatic carboxylic acid cosurfactant;

(d) 0.4 to 10% of a water insoluble hydrocarbon, essential oil or perfume;

(e) 0.05% to 5.0% of an acaricidal agent selected from the group consisting of:

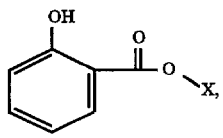

wherein

X = 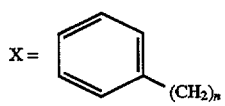

or a $C_6$–$C_{14}$ alkyl group, wherein n=1 to 3;

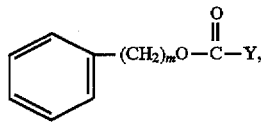

wherein m=1 to 3 and Y is a $C_1$–$C_6$ alkyl group,

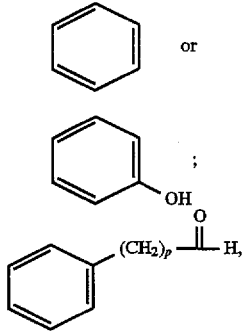

wherein p=1 to 3; and carvone;

(f) 0 to 15% of magnesium sulfate heptahydrate; and (g) the balance being water, wherein the composition does not contain a solid component having a mean particle size of 2 to 100 microns and wherein 50 to 70 wt. % of the essential oil or perfume may exhibit acaricidal activity.

12. A liquid crystal composition comprising approximately by weight: 0 to 20% of an anionic surfactant, wherein the anionic surfactant is selected from the group consisting of sulfonate and sulfate surfactants; 1% to 20% of a glycol ether or a $C_3$–$C_6$ aliphatic carboxylic acid cosurfactant; 0% to 2.5% of a fatty acid; 0.1% to 20% of an ethoxylated nonionic surfactant or a mixture of

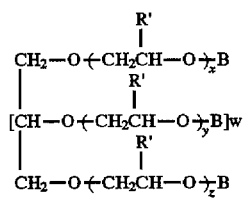 (I)

and

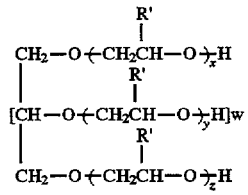 (II)

wherein w equals one to four; B is selected from the group consisting of hydrogen and a group represented by:

wherein R is selected from the group consisting of alkyl group having 6 to 22 carbon atoms, and alkenyl groups having 6 to 22 carbon atoms, wherein at least one of the B groups is represented by said

R' is selected from the group consisting of hydrogen and methyl groups; x, y and z have a value between 0 and 60, provided that (x+y+z) equals 2 to 100, wherein in Formula (I) the weight ratio of monoester/diester/triester is 45 to 90/5 to 40/1 to 20, wherein the weight ratio of Formula (I) to Formula (II) is a value between 3 and 0.02; 0.05% to 5.0% of an acaricidal agent selected from the group consisting of:

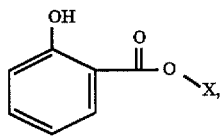

wherein

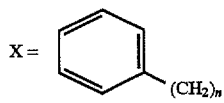

or a $C_6$–$C_{14}$ alkyl group, wherein n=1 to 3;

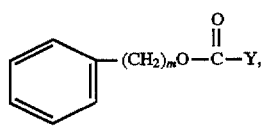

wherein m=1 to 3 and Y is a $C_1$–$C_6$ alkyl group,

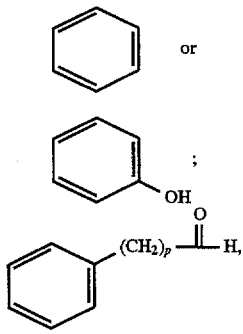

wherein p=1 to 3; and carvone; 0.5% to 10% of a water insoluble hydrocarbon, essential oil or a perfume and the balance being water, wherein the composition does not contain a solid component having a mean particle size of 2 to 100 microns and wherein 50 to 70 wt. % of the essential oil or perfume may exhibit acaricidal activity.

13. An all purpose liquid cleaning composition comprising approximately by weight:

(a) 0.1% to 20% of an ethoxylated nonionic surfactant or mixture of

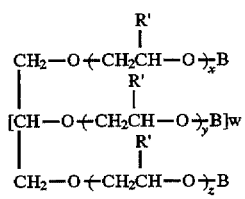

and

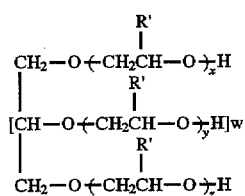

wherein w equals one to four; B is selected from the group consisting of hydrogen and a group represented by:

wherein R is selected from the group consisting of alkyl group having 6 to 22 carbon atoms, and alkenyl groups having 6 to 22 carbon atoms, wherein at least one of the B groups is represented by said

R' is selected from the group consisting of hydrogen and methyl groups; x, y and z have a value between 0 and 60, provided that (x+y+z) equals 2 to 100, wherein in Formula (I) the weight ratio of monoester/diester/triester is 45 to 90/5 to 40/1 to 20, wherein the weight ratio of Formula (I) to Formula (II) is a value between 3 and 0.02;

(b) 0 to 20% of a glycol ether or a $C_3$–$C_6$ aliphatic carboxylic acid cosurfactant;

(c) 0 to 1% of a perfume, essential oil or water insoluble hydrocarbon;

(d) 0 to 20% of an anionic surfactant, wherein the anionic surfactant is selected from the group consisting of sulfonate and sulfate surfactants;

(e) 0.05% to 5.0% of an acaricidal agent selected from the group consisting of:

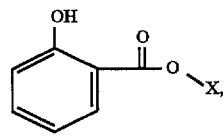

wherein

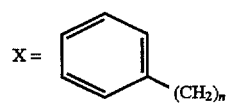

or a $C_6$–$C_{14}$ alkyl group, wherein n=1 to 3;

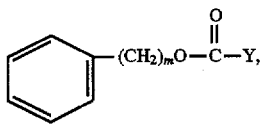

wherein m=1 to 3 and Y is a $C_1$–$C_6$ alkyl group,

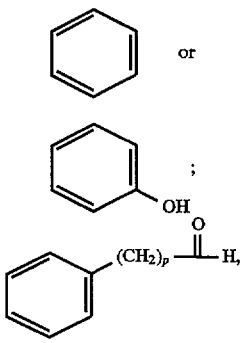

wherein p=1 to 3; and carvone; and (f) the balance being water, wherein the composition does not contain a solid component having a mean particle size of 2 to 100 microns and wherein 50 to 70 wt. % of the essential oil or perfume may exhibit acaricidal activity.

14. A light duty liquid composition comprising approximately by weight:

(a) 10% to 40% of at least one organic compound selected from the group consisting of anionic surfactants, zwitterionic surfactants, nonionic surfactants formed from the condensation product of a fatty alcohol and ethylene oxide and/or propylene oxide, and a mixture of

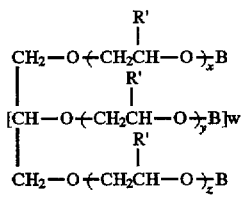 (I)

and

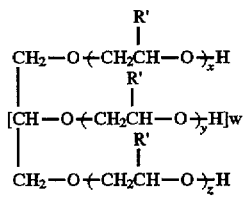 (II)

wherein w equals one to four; B is selected from the group consisting of hydrogen and a group represented by:

wherein R is selected from the group consisting of alkyl group having 6 to 22 carbon atoms, and alkenyl groups having 6 to 22 carbon atoms, wherein at least one of the B groups is represented by said

R' is selected from the group consisting of hydrogen and methyl groups; x, y and z have a value between 0 and 60, provided that (x+y+z) equals 2 to 100, wherein in Formula (I) the weight ratio of monoester/diester/triester is 45 to 90/5 to 40/1 to 20; wherein the weight ratio of Formula (I) to Formula (II) is a value between 3 and 0.02 and mixtures thereof;

(b) 0.05% to 5.0% of an acaricidal agent selected from the group consisting of:

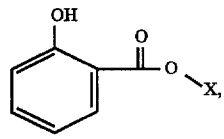

wherein

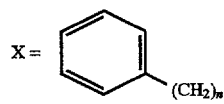

or a $C_6$–$C_{14}$ alkyl group, wherein n=1 to 3;

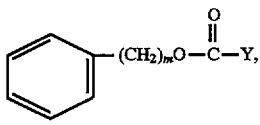

wherein m=1 to 3 and Y is a $C_1$–$C_6$ alkyl group,

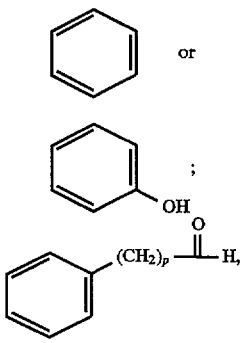

wherein p=1 to 3; and carvone;

(c) 0.1% to 10% of a solubilizer;

(d) 0 to 1.0% of a perfume; and (e) the balance being water, wherein the composition does not contain a solid component having a mean particle size of 2 to 100 microns and wherein 50 to 70 wt. % of the essential oil or perfume may exhibit acaricidal activity.

* * * * *